US012654854B2

(12) United States Patent
　　　Tamir

(10) Patent No.:　US 12,654,854 B2
(45) Date of Patent:　　Jun. 16, 2026

(54) DEVICE FOR RELEASING INSECTS FROM AN AERIAL VEHICLE AND USE THEREOF

(71) Applicant: Yair Tamir, Tel Aviv (IL)

(72) Inventor: Yair Tamir, Tel Aviv (IL)

( * ) Notice: Subject to any disclaimer, the term of this patent is extended or adjusted under 35 U.S.C. 154(b) by 180 days.

(21) Appl. No.: 18/237,701

(22) Filed: Aug. 24, 2023

(65) Prior Publication Data

US 2023/0406500 A1　　Dec. 21, 2023

Related U.S. Application Data

(63) Continuation of application No. PCT/IL2022/050291, filed on Mar. 15, 2022.

(60) Provisional application No. 63/161,485, filed on Mar. 16, 2021.

(51) Int. Cl.
　　　*B64D 1/18*　　　(2006.01)
　　　*A01K 67/31*　　　(2025.01)
(52) U.S. Cl.
　　　CPC .............. *B64D 1/18* (2013.01); *A01K 67/31* (2025.01)
(58) Field of Classification Search
　　　CPC .................................. A01K 67/31; B64D 1/18
　　　See application file for complete search history.

(56) References Cited

U.S. PATENT DOCUMENTS 3,484,062 A * 12/1969 Johnson ................... B64D 1/16
　　　　　　　　　　　　　　　　　　　　　　169/53
3,777,978 A * 12/1973 Manicatide ............. A01M 9/00
　　　　　　　　　　　　　　　　　　　　　　267/136

4,260,108 A * 4/1981 Maedgen, Jr. ........... B64D 1/18
　　　　　　　　　　　　　　　　　　　　　　222/161
(Continued)

FOREIGN PATENT DOCUMENTS

KR　　20110009066 U　　9/2011
KR　　20180062624 A　　6/2018
KR　　　102090279 B1　　3/2020

OTHER PUBLICATIONS

PCT International Search Report for International Application No. PCT/IL2022/050291, mailed Jun. 27, 2022, 3pp.
(Continued)

*Primary Examiner* — Magdalena Topolski
(74) *Attorney, Agent, or Firm* — The Roy Gross Law Firm, LLC; Roy D. Gross

(57) ABSTRACT

There is provided herein a device for releasing insects from an aerial vehicle, the device comprising: an insect lodging chamber configured to hold insects, the chamber comprising a chamber wall defining an inner volume of the chamber, a chamber inlet, a chamber outlet and a rotating valve associated with the chamber outlet, the rotating valve comprises a plurality of wings configured to rotate around a central longitudinal axis of the rotating valve and thereby to release the insects portion by portion; an insect dispersion unit comprising: a converging air duct comprising an air flow inlet and an air flow outlet, wherein the chamber outlet is connected to a converged section of air duct, such that air flowing from air flow inlet to air flow outlet creates a pressure drop, which induces suction of insects from chamber, through chamber outlet, into air duct and out of the device through air flow outlet; and a controller functionally associated with the rotating valve, for controlling the rate of rotation thereof.

15 Claims, 11 Drawing Sheets

(56) References Cited

U.S. PATENT DOCUMENTS

| 5,148,989 | A | * | 9/1992 | Skinner | .................... | B64D 1/18 |
| | | | | | | 239/128 |
| 5,794,847 | A | * | 8/1998 | Stocker | ................. | A01N 63/14 |
| | | | | | | 239/654 |
| 2019/0092471 | A1 | | 3/2019 | Lepek et al. | | |

OTHER PUBLICATIONS

PCT Written Opinion for International Application No. PCT/IL2022/050291, mailed Jun. 27, 2022, 8pp.

* cited by examiner

DEVICE FOR RELEASING INSECTS FROM AN AERIAL VEHICLE AND USE THEREOF

CROSS REFERENCE TO RELATED APPLICATIONS

This application is a Bypass Continuation of PCT Patent Application No PCT/IL2022/050291 having International filing date of Mar. 15, 2022, which claims the benefit of priority of U.S. Provisional Patent Application No. 63/161, 485, filed Mar. 16, 2021, the contents of which are all incorporated herein by reference in their entirety.

FIELD OF THE INVENTION

There is provided herein a device for releasing insects from an aerial vehicle and use thereof for, storing insects under optimal viability conditions and dispersing the insects at predetermined locations.

BACKGROUND OF THE INVENTION

Large areas used worldwide for agriculture are exposed to damages caused by pests which pose a serious economic threat to farmers. Use of natural predators, relative to the pest, such as, pesticides to manage pest problems, also known as biological control, is a common practice around the world, due to its efficiency and beneficial cost per value.

One of the current problems with the dispersion of living insects or larvae is the dispersion rate and the mortality rate. Dispensing insects by hand is a gentle but labor-intensive method while mechanical/automatic dispensing is difficult to accomplish without harming or killing the living insects.

There is an unmet need for devices for dispersing insects while maintaining insects' viability and further enabling storage and dispersion of large quantities of insects.

SUMMARY OF THE INVENTION

There is provided herein, in accordance with some embodiments, a device for accommodating and releasing insects from an aerial vehicle, a system comprising the device, and methods for controlled dispersion of insects from the device.

As detailed below, the device has an insect lodging chamber, which includes one or more shelves (e.g., two, three, four or more shelves). Each shelf is attached, at a first end thereof, to an inner surface of a chamber wall, and can move from an expanded configuration to a closed (folded) configuration. Advantageously, when a shelf is in an expanded configuration, the shelf extends across the chamber; however, a second end of said shelf does not contact an opposing inner surface of the chamber. Thus, the insects can, on the one hand, scatter (essentially homogeneously) between two sections of the chamber formed by the shelf and, and on the other hand, are free to move between the sections. When the shelf is in a closed (folded) configuration, the insects can move freely between the two sections formerly formed when the shelf was expanded.

Advantageously, each shelf is independently designed to be moved by a controllable mechanism that is adapted to alter the shelf configuration from an expanded configuration to a folded configuration and vice versa, as needed, based on the number of insects present in the insect lodging chamber. According to some embodiments, the shelf movement may be conducted gently to avoid damaging the insects within a chamber during shelf movement, for example, by controlling the rate of change in configuration. According to some embodiments, both the expanded configuration and the folded configuration are designed to avoid squashing, or crushing, insects between the shelf and the inner wall of the chamber.

According to some embodiments, the device further includes an insect dispersion unit configured to disperse the insects stored in the insect lodging chamber.

Advantageously, the insect dispersion unit is structured to facilitate dispersion of the insects utilizing the venturi effect, thus avoiding or minimizing contact of the insects with moving parts of the device, thereby maintaining the vitality of the insects and avoid damaging them during dispersion.

There is provided, according to some embodiments, a device for releasing insects from an aerial vehicle, the device comprising:

an insect lodging chamber configured to hold insects, the chamber comprising a chamber wall defining an inner volume of the chamber, a chamber inlet, a chamber outlet and one or more movable shelves, each shelf is attached, at a first end thereof, to an inner surface of the chamber wall, wherein each shelf has an expanded configuration and a folded configuration, wherein in the expanded configuration a shelf is extended across the chamber, such that a second end of said shelf does not contact an opposing inner surface of the chamber;

an insect dispersion unit comprising:

a converging air duct comprising an air flow inlet and an air flow outlet, wherein the chamber outlet is connected to a converged section of air duct, such that air flowing from air flow inlet to air flow outlet creates a pressure drop, which induces suction (venturi effect) of insects from chamber, through chamber outlet, into air duct and out of the device through air flow outlet; and a controller functionally associated with each shelf, for controlling the configuration thereof;

According to some embodiments, the diameter of the air flow outlet is smaller than the diameter of the air flow inlet.

According to some embodiments, the converging air is a tube structure having a first section with a first cross section area and a second section with a second cross section area, wherein the first section is upstream to the second section and the first cross section area is larger than the second cross section area.

According to some embodiments, the device further comprises a separating element configured to block or unblock chamber outlet and a motor associated therewith for controlling the separating element so as to determine the size of an opening between the chamber and the air duct.

According to some embodiments, the chamber outlet is connected to converged section via a chamber-to-duct passage.

According to some embodiments, the device further comprises a compressor located in, or in proximity to, air flow inlet for producing air flow from air flow inlet to air flow outlet.

According to some embodiments, the device further comprises a temperature regulating unit for cooling the temperature of the chamber.

According to some embodiments, the controller is further configured to control separating element, compressor and/or temperature regulating unit.

According to some embodiments, the device further comprises a navigation system and/or an interface for communicating with a navigation system, for determining the location of the device and/or for controlling the operation of the device based on the location determined.

According to some embodiments, the device further comprises a communication interface.

According to some embodiments, at least one of the one or more movable shelves is attached, at a first end thereof, to an inner surface of the chamber wall through a controllable mechanism.

According to some embodiments, at least one of the one or more movable shelves is designed to fold down along the chamber walls when the at least one shelf is shifted to a folded configuration.

According to some embodiments, at least one shelf of the one or more movable shelves is a telescopic shelf comprising a plurality of sections designed to slide into/on one another when the telescopic shelf is shifted to a folded configuration.

According to some embodiments, the chamber wall is coated with a thermal coating.

There is provided, according to some embodiments, a system for releasing insects from an aerial vehicle, the system comprising:

a device for releasing insects from an aerial vehicle, the device comprising an insect lodging chamber configured to hold insects, the chamber comprising a chamber wall defining an inner volume of the chamber, a chamber inlet, a chamber outlet and a one or more of movable shelves, each shelf is attached, at a first end thereof, to an inner surface of the chamber wall, wherein each shelf has an expanded configuration and a folded configuration, wherein in the expanded configuration a shelf is extended across the chamber, such that a second end of said shelf does not contact an opposing inner surface of the chamber;

an insect dispersion unit comprising:

a converging air duct comprising an air flow inlet and an air flow outlet, wherein the chamber outlet is connected to a converged section of air duct, such that air flowing from air flow inlet to air flow outlet creates a pressure drop, which induces suction of insects from chamber, through chamber outlet, into air duct and out of the device through air flow outlet; and a controller functionally associated with each shelf, for controlling the configuration thereof; and an unmanned aerial vehicle.

There is provided, according to some embodiments, a method for releasing insects from an aerial vehicle, the method comprising:

providing the device disclosed herein;

loading insect into the insect lodging chamber; and utilizing a controller:

activating the compressor, facilitating passage of insects between the chamber outlet and the converged section of the air duct, thereby creating a venturi effect, which induces suction of insects from the insect lodging chamber, through the chamber outlet, into the air duct and out of the device through the air flow outlet; and shifting at least one of the one or more shelves from an expanded configuration to a folded configuration, upon indication of a reduction in insect density in the chamber.

There is further provided, according to some embodiments, a device for releasing insects from an aerial vehicle, the device comprising:

an insect lodging chamber configured to hold insects, the chamber comprising a chamber wall defining an inner volume of the chamber, a chamber inlet, a chamber outlet and a rotating valve associated with the chamber outlet, the rotating valve comprises a plurality of wings configured to rotate around a central longitudinal axis of the rotating valve and thereby to release the insects portion by portion;

an insect dispersion unit comprising:

a converging air duct comprising an air flow inlet and an air flow outlet, wherein the chamber outlet is connected to a converged section of air duct, such that air flowing from air flow inlet to air flow outlet creates a pressure drop, which induces suction of insects from chamber, through chamber outlet, into air duct and out of the device through air flow outlet; and a controller functionally associated with the rotating valve, for controlling the rate of rotation thereof.

According to some embodiments, the diameter of the air flow outlet is smaller than the diameter of the air flow inlet. According to some embodiments, the converging air is a tube structure having a first section with a first cross section area and a second section with a second cross section area, wherein the first section is upstream to the second section and the first cross section area is larger than the second cross section area.

According to some embodiments, the plurality of wings are configured to release a first portion of insects located between a first pair of adjacent wings and, upon rotation of the rotating valve, to release a second portion of insects located between a second pair of adjacent wings.

According to some embodiments, the device further includes a motor associated with the rotating valve and configured for controlling the rotating valve so as to determine the rate of rotation.

According to some embodiments, the chamber outlet is connected to converged section via a chamber-to-duct passage.

According to some embodiments, the device further includes a compressor located in, or in proximity to, air flow inlet for producing air flow from air flow inlet to air flow outlet. According to some embodiments, the device further includes one or more temperature regulating units for cooling the temperature of the chamber. According to some embodiments, the controller is further configured to control the compressor and/or the one or more temperature regulating unit.

According to some embodiments, the device further includes a navigation system and/or an interface for communicating with a navigation system, for determining the location of the device and/or for controlling the operation of the device based on the location determined. According to some embodiments, the device further includes a communication interface. According to some embodiments, the chamber wall is coated with a thermal coating.

There is further provided, according to some embodiments, a system for releasing insects from an aerial vehicle, the system comprising:

a device for releasing insects from an aerial vehicle, the device comprising:

an insect lodging chamber configured to hold insects, the chamber comprising a chamber wall defining an inner volume of the chamber, a chamber inlet, a chamber outlet and a rotating valve associated with the chamber outlet, the rotating valve comprises a plurality of wings configured to rotate around a central longitudinal axis of the rotating valve and thereby to release the insects portion by portion;

an insect dispersion unit comprising:

a converging air duct comprising an air flow inlet and an air flow outlet, wherein the chamber outlet is connected to a converged section of air duct, such that air flowing from air flow inlet to air flow outlet creates a pressure drop, which induces suction of insects from chamber, through chamber outlet, into air duct and out of the device through air flow outlet; and a controller functionally associated with the rotating valve, for controlling the rate of rotation thereof; and an unmanned aerial vehicle.

There is further provided, according to some embodiments, a method for releasing insects from an aerial vehicle, the method comprising: providing a device according to any of the embodiments disclosed herein, loading insect into the insect lodging chamber, and, utilizing a controller: activating the compressor, and rotating the rotating valve, thereby facilitating passage of portions of insects between the chamber outlet and the converged section of the air duct, thereby creating a venturi effect, which induces suction of insects from the insect lodging chamber, through the chamber outlet, into the air duct and out of the device through the air flow outlet.

Other objects, features and advantages of the present invention will become clear from the following description, examples and drawings.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not to scale. In the Figures.

DETAILED DESCRIPTION

Figures 1A, 1B:
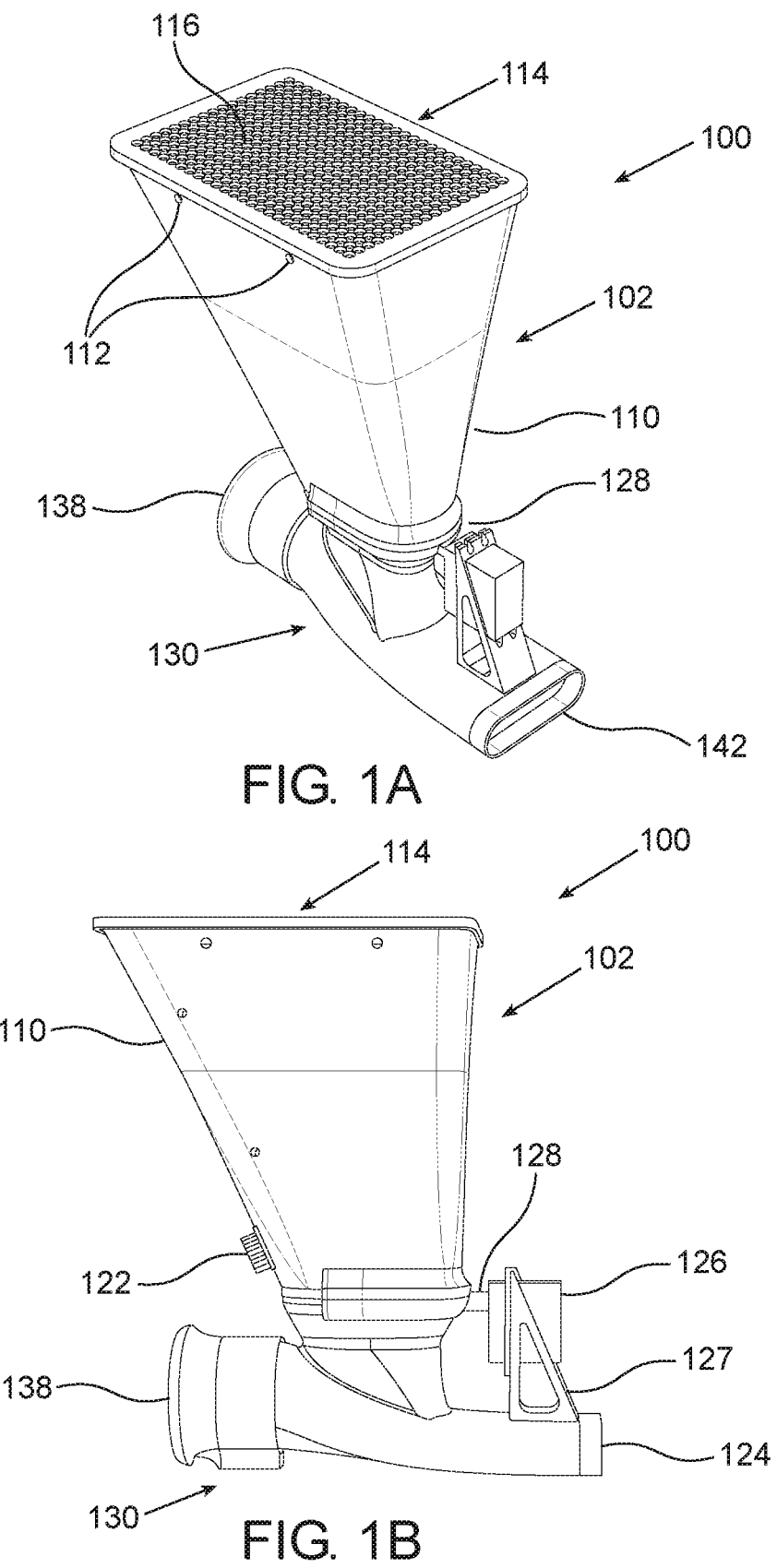
FIGS. 1A-1D schematically depict different views of a device for releasing insects from an aerial vehicle, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In the figures, like reference numerals refer to like parts.

Throughout the figures of the drawings, different superscripts for the same reference numerals may be used to denote different embodiments of the same elements. Embodiments of the disclosed devices and systems may include any combination of different embodiments of the same elements. Specifically, any reference to an element without a superscript may refer to any alternative embodiment of the same element denoted with a superscript. Components having the same reference number followed by different lowercase letters may be collectively referred to by the reference number alone. If a particular set of components is being discussed, a reference number without a following lowercase letter may be used to refer to the corresponding component in the set being discussed. In order to avoid undue clutter from having too many reference numbers and lead lines on a particular drawing, some components will be introduced via one or more drawings and not explicitly identified in every subsequent drawing that contains that component.

Reference is now made to FIGS. 1A to 1D, which schematically depict different views of a device 100 for releasing insects from an aerial vehicle, according to some embodiments. Device 100 includes an insect lodging chamber 102 configured to hold insects prior to and/or during the scattering process. Chamber 102 includes chamber wall(s) 110 defining an inner volume of chamber 102, a chamber inlet 114, at a top section thereof, configured for loading the insects, a chamber outlet 128, at a bottom section thereof, configured for insects exit, and one or more movable shelves 120 (shown in FIGS. 2A-C).

Device 100 further includes an electric circuitry (not shown) functionally associated with each shelf 120, for controlling the configuration of each shelf.

Device 100 further includes an insect dispersion unit 130 comprising a converging air duct 134 having an air flow inlet 138 and an air flow outlet 142. Chamber outlet 128 is connected to a converged section 136 of air duct 134, such that air flowing from air flow inlet 138 to air flow outlet 142 creates a pressure drop (venturi effect), which induces suction of insects from chamber 102, through chamber outlet 128, into air duct 134 and out of the device through air flow outlet 142. Insect dispersion unit 130 further includes a compressor 140 located in, or in proximity to, air flow inlet 138 for producing (additional) air flow from air flow inlet 138 to air flow outlet 142.

According to some embodiments, chamber outlet 128 is connected to convergent section 136 via a chamber-to-duct passage 133.

It is to be understood, without bounding to any theory, that the effect inducing the insect exiting the device is the venturi effect. In brief, in fluid dynamics the velocity of a fluid (or gas) must increase as it passes through a constriction while its static pressure must decrease. Hence, any gain of kinetic energy that the fluid (or gas) may attain by its increased velocity through a constriction (e.g., converged section 136 of air duct 134) is balanced by a drop in pressure, which forms the venturi effect and results in suction of the insects out of the device and into the environment.

According to some embodiments, chamber inlet 114 is covered by a porous cover 116. Porous cover 116 enables exchange of oxygen/air between chamber 102 and the environment.

According to some embodiments, insect lodging chamber 102 may be integrally formed with or connected to insect dispersion unit 130.

Figures 1C, 1D:
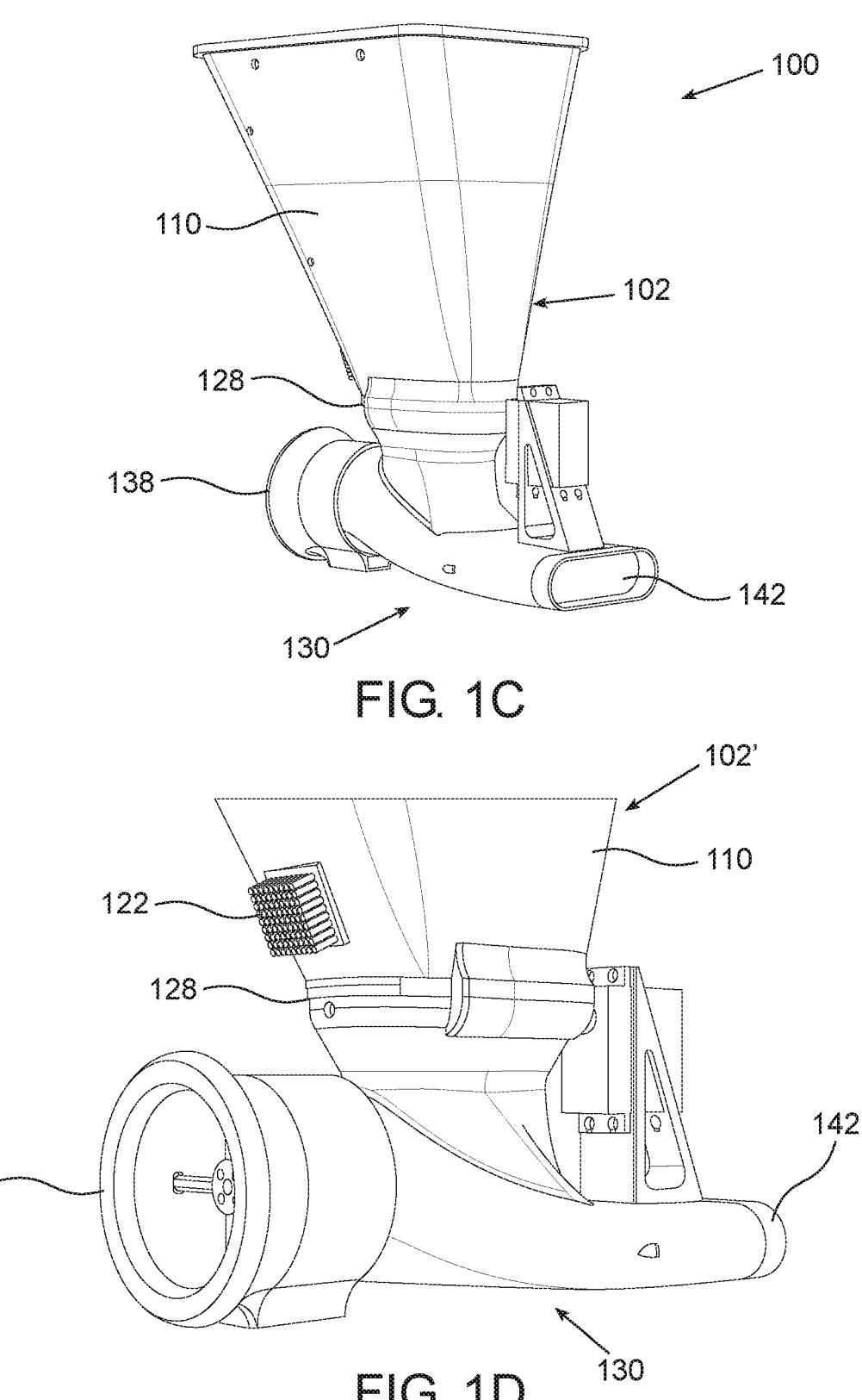

According to some embodiments, insect lodging chamber 102 may be modular, such that various sizes of chamber 102 can be assembled to dispersion unit 130 in order to form device 100, based on the requirement. For example, for small insects and/or a small number of insects and/or for dispersion over a relatively small area, a smaller chamber 102' can be used, as demonstrated in FIG. 1D, compared to the size of chamber 102 which may be used for larger insects and/or a larger number of insects and/or for dispersion over a large area, as demonstrated in FIGS. 1A to 1C.

According to some embodiments, device 100 may further include a temperature regulating unit 122 configured to regulate the temperature in chamber 102 (e.g., cool as needed). According to some embodiments, temperature regulating unit 122 may include a Peltier module or any other cooling/heating element(s).

According to some embodiments, device 100's temperature regulating unit 122 includes one or more temperature sensors (not shown) configured to monitor the temperature within device 100 and particularly within chamber 102, such that when a temperature above/below a desired temperature (range) is detected, temperature regulating unit 122 cools/heats chamber 102 respectively.

According to some embodiments, temperature regulating unit 122 may be integrated into the walls of chamber 102.

According to some embodiments, chamber wall 110 may be coated with a thermal coating configured to provide some degree of thermal insulation between chamber 102 and the environment, thereby maintaining a desired temperature within chamber 102.

According to some embodiments, device 100 further comprises a plurality of elements/orifices 112, located on chamber wall 110 and configured to reversibly attach device 100 to an aerial vehicle 150, as further discussed below with respect to FIG. 4.

Figure 2A:
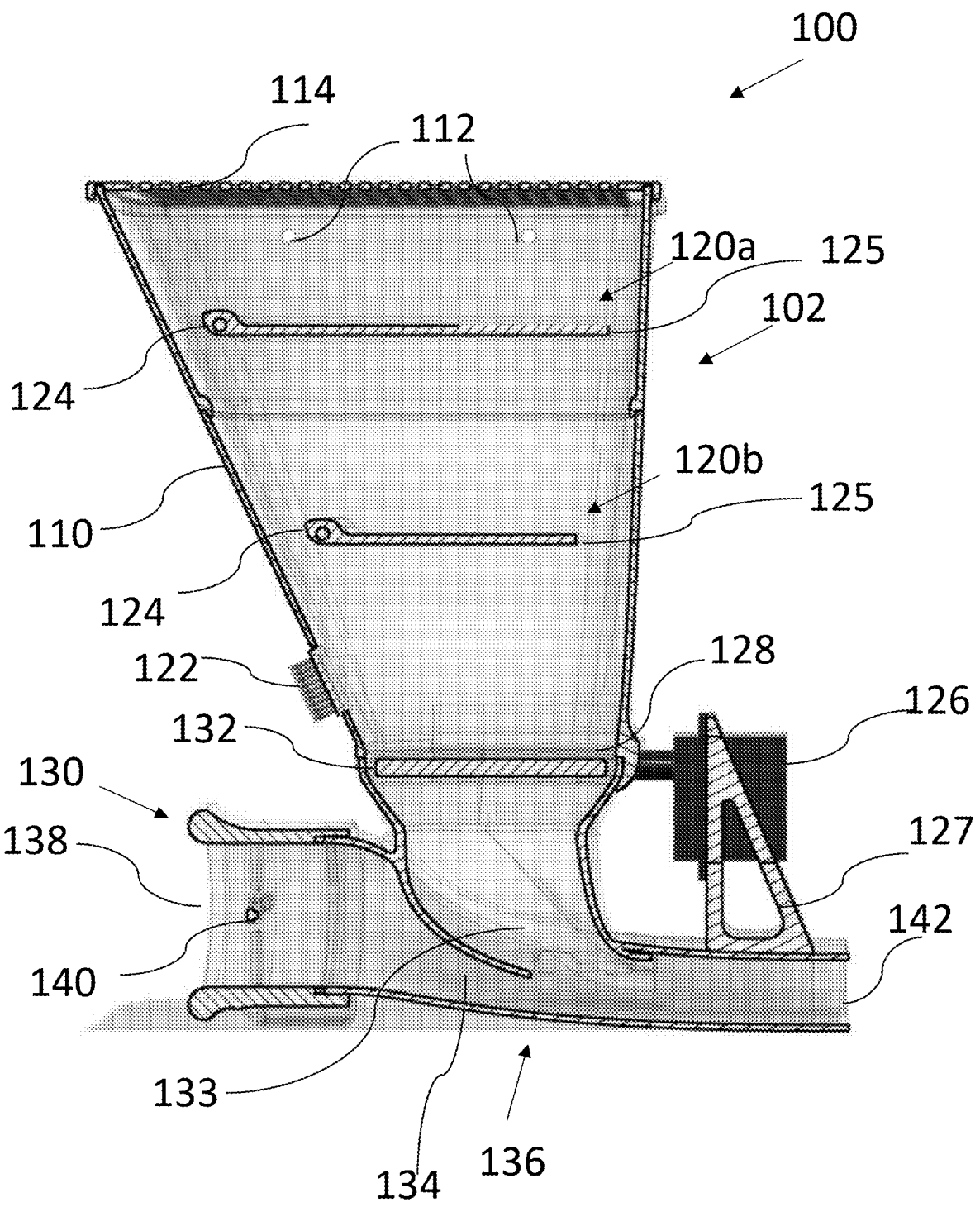
FIGS. 2A-2C schematically depict different views of the device for releasing insects from an aerial vehicle, in a "transparent" presentation, according to some embodiments.
Figure 2B:
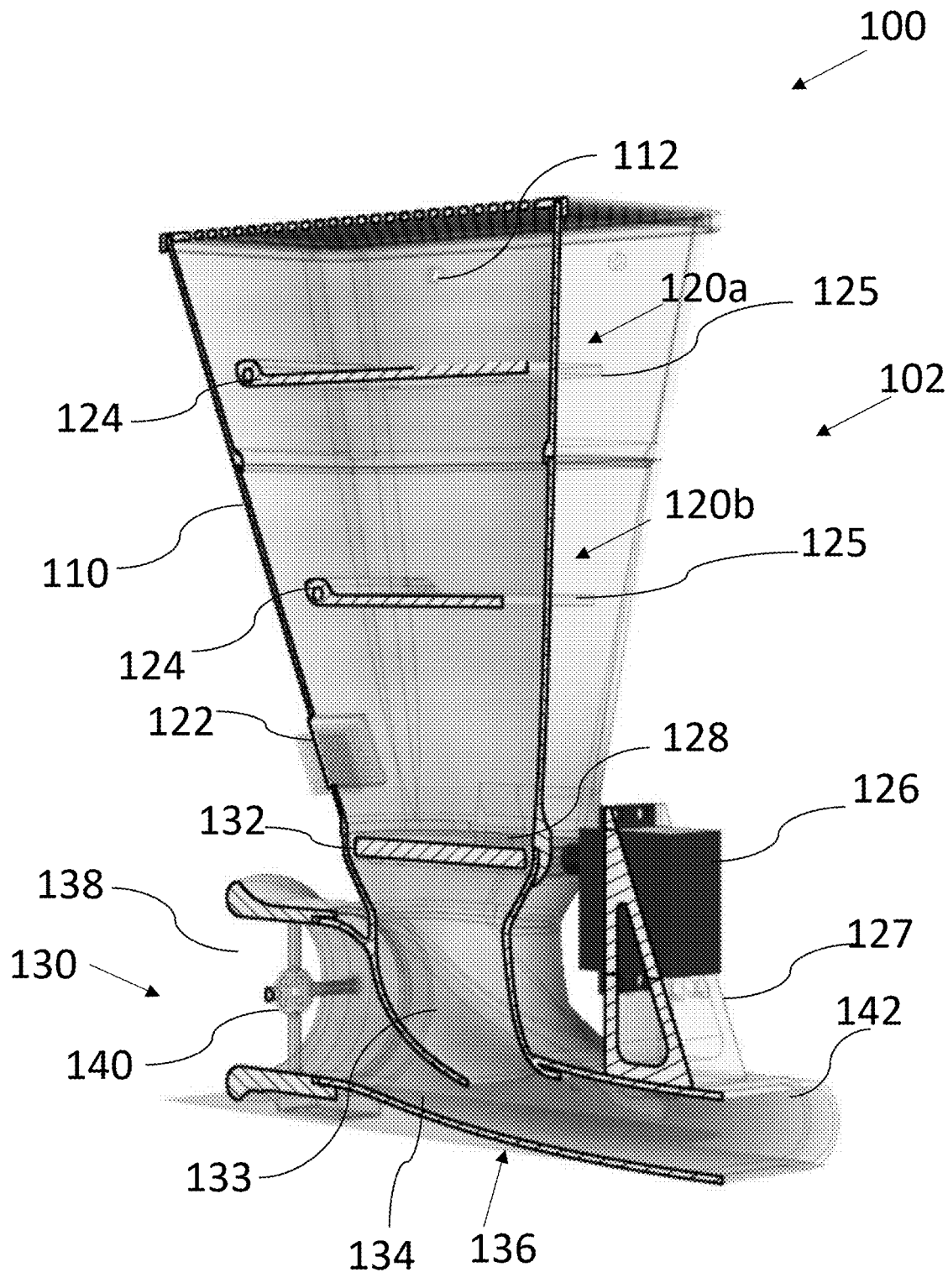
Figure 2C:
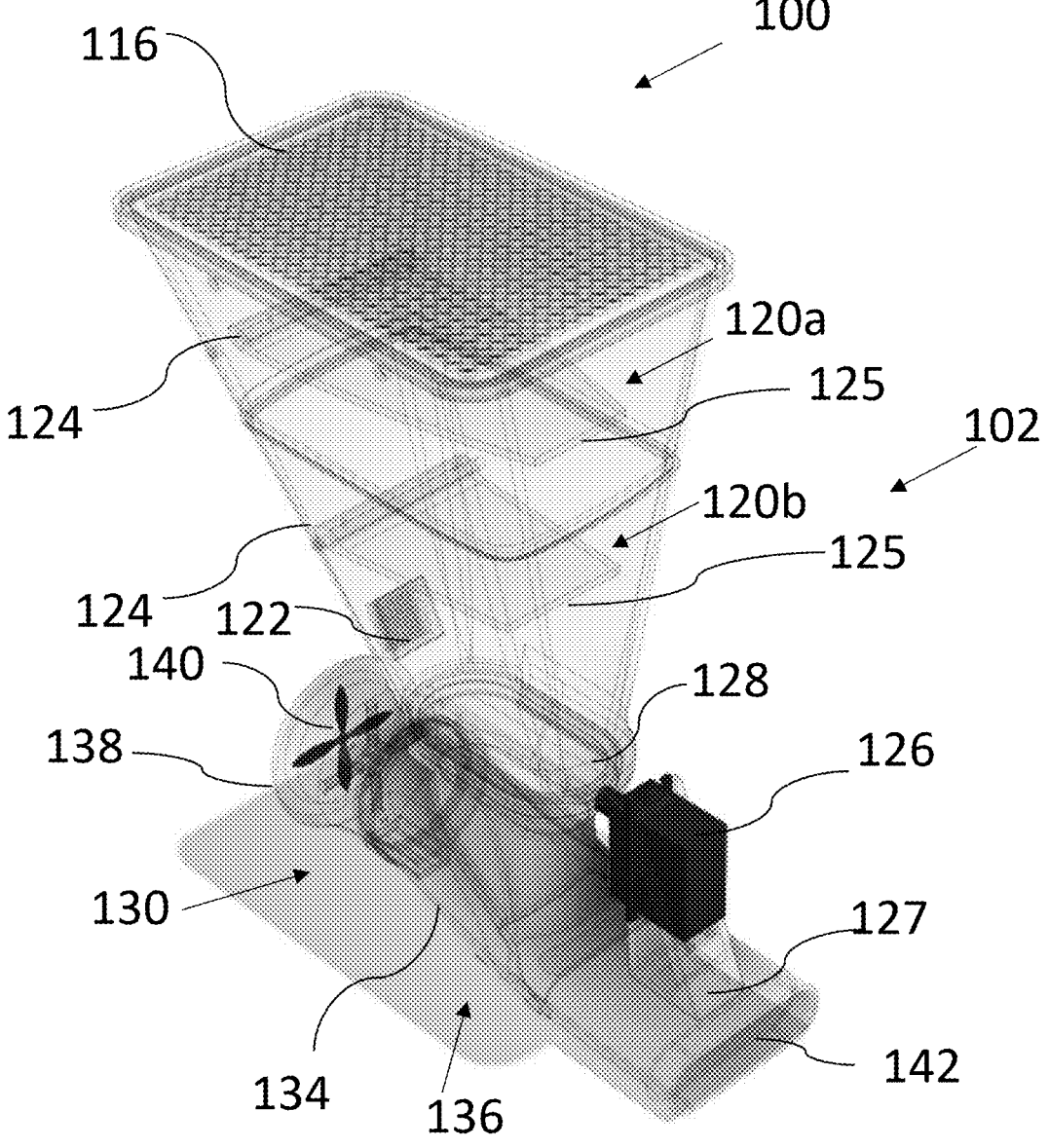

Reference is now made to FIGS. 2A-C, which schematically depict different views of the device in a "transparent" presentation, according to some embodiments.

Device 100 includes one or more (shown herein as two but may be more) movable shelves 120a and 120b (collectively, 120). Each shelf is attached, at a first end (124) thereof, to an inner surface of the chamber wall, wherein each shelf has an expanded configuration and a folded configuration. According to some embodiments, the attachment of first end 124 of shelves 120a and 120b to the chamber wall may be in the form of a hinge, a pivot joint, a knuckle joint among other suitable options and may be operated by a controllable mechanism. In an expanded configuration (as shown in FIGS. 2A-C) each of shelves 120a and 120b extend across the chamber, such that second ends (125) of shelves 120a and 120b do not contact an opposing inner surface of chamber 102.

According to some embodiments, each of movable shelves 120a and 120b can independently shift from an expanded configuration to folded configuration by any suitable mechanism. For example, according to some embodiments, each movable shelf 120a/b changes from expanded configuration to folded configuration by folding down, e.g., folding towards dispersion unit 130. Folding down of movable shelves 120a and 120b may be controlled by a controller and may be performed at slow rate.

According to some embodiments, each of movable shelves 120a and 120b may be a telescopic comprising a plurality of sections (vertebrate) designed to slide into, or on, one another when the telescopic shelf is shifted from an expanded configuration to a folded configuration. The rate of sliding into, or on, of the plurality of sections (vertebrate) may be controlled by a controller and may be performed at a slow rate.

Movable shelves 120a and 120b are designed for compartmentalizing chamber 102 thereby allowing the insects to be scattered within the compartments of chamber 102 rather than to be compressed in over-populating one region of chamber 102. This structure enables to load device 100 with a large number of insects, while maintaining the insects within chamber 102 under optimal conditions for good viability. Compartmentalization is achieved even though movable shelves 120a and 120b are not fully extended between two parallel inner walls of chamber 102. The space that remains between the second inner wall and an edge (second ends 125) of movable shelf 120a and 120b in expanded configurate allows certain transition of insects between compartments. Such transition is typically minimal and does not create regions where insects are in compressed conditions.

The number of compartments defined by movable shelves 120 is determined by the number of movable shelves 120 within chamber 102, which depends on the number of insects required to be dispersed and/or the size of insects stored within chamber 102. As shown herein, device 100 includes movable shelves 120. According to some embodiments, device 100 may include at least three movable shelves 120. According to other embodiments, device 100 may include at least four movable shelves 120.

According to some embodiment, transformation of shelf 120 from an expanded configuration to a folded configuration is carried out at a slow rate, such as, between about 1-10 mm/sec to about 8 mm/sec or between about 2 mm/sec to about 8 mm/sec.

Advantageously, the transition between expanded to folded configurations is designed such that it performs minimal impact on the insects stored within chamber 102 and is aimed at maintaining their viability. As detailed below, this goal is achieved by enabling the transition only when there is minimal to zero contact between the movable shelves 120 and the insects.

According to some embodiments, "Folding down" of movable shelves 120 as used herein refer to changing the angle between shelf 120 and chamber wall 110 from about 900 to above 0°, while avoiding crushing insects between the folded shelf and the chamber wall. According to some embodiments, in a folded configuration the angle between shelf 120 and chamber wall 110 is at least 5°. According to some embodiments, in folded configuration the angle between shelf 120 and chamber wall 110 is at least 10°. According to some embodiments, in folded configuration the angle between shelf 120 and chamber wall 110 is at least 15°. According to some embodiments, in folded configuration the angle between shelf 120 and chamber wall 110 is about 20°.

As used herein, the term "about" may be used to specify a value of a quantity or parameter (e.g., angle, length, distance, height) within a continuous range of values in the neighborhood of (and including) a given (stated) value. According to some embodiments, "about" may specify the value of a parameter to be between 80% and 120% of the given value. For example, the statement "the angle is equal to about 10°" is equivalent to the statement "the length of the element is between 8° m and 12°". According to some embodiments, "about" may specify the value of a parameter to be between 90% and 110% of the given value. According to some embodiments, "about" may specify the value of a parameter to be between 95% and 105% of the given value.

The terms "sliding into" and "sliding on" are interchangeable and refer to the shortening (folding-in) of movable shelves 120 having a telescopic structure, during transition from expanded configuration to folded configuration. According to some embodiments, folding-in shortens movable shelf 120 by at least 10% relative to its original length in an expanded configuration. According to some embodiments, folding-in shortens movable shelf 120 by at least 20% relative to its original length in an expanded configuration. According to some embodiments, folding-in shortens movable shelf 120 by at least 30% relative to its original length in an expanded configuration. According to some embodiments, folding-in shortens movable shelf 120 by at least 40% relative to its original length in an expanded configuration. According to some embodiments, folding-in shortens movable shelf 120 by at least 50% relative to its original length in an expanded configuration. According to some embodiments, folding-in shortens movable shelf 120 by at least 60% relative to its original length in an expanded configuration.

According to some embodiments, device 100 may further include at least one density sensor (not shown) configured to calculate the occupancy of chamber 102 by the insects stored therein. According to some embodiments, the at least one density sensor is configured to calculate the presence of insects in contact with each shelf 120. According to some embodiments, the density sensor is associated with the controller and/or with the shelves' controllable mechanism such that, when said at least one density sensor senses a density of insects below a predetermined density threshold, it enables transformation of shelf 120 from an expanded configuration to a folded configuration.

It is to be understood that the density sensor operates as long as device 100 stores and disperses insects. Hence, should the density of insects in the vicinity of a shelf increase above the predetermined density threshold, during transition of said shelf from expanded to close configuration, the transition is halted. Thus, the density sensor may provide a safety mechanism during operation, by enabling change in shelf configuration only under appropriate conditions, namely, only under minimum damage, or no damage, to the insects stored in chamber 102.

Figure 2D:
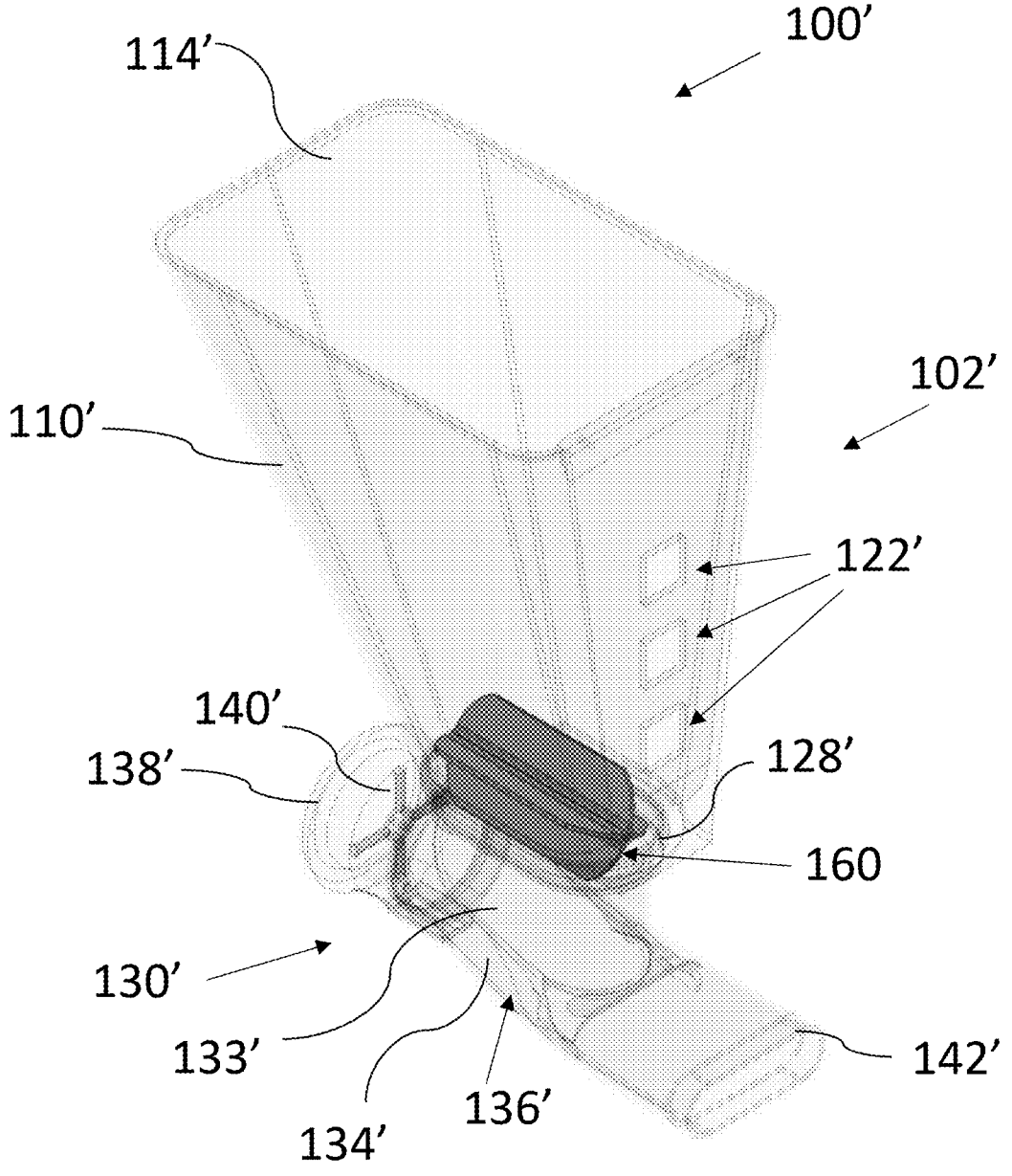
FIG. 2D schematically depict an isometric view of a device for releasing insects from an aerial vehicle, in a "transparent" presentation, according to additional/or alternative embodiments.

Reference is now made to FIG. 2D, schematically depict an isometric view of another/alternative configuration of a device 100' for releasing insects from an aerial vehicle, in a "transparent" presentation, according to additional or alternative embodiments.

The main difference between device 100 and device 100' is that device 100' does not include separating element 132 but rather includes a rotating valve 160. Rotating valve 160 includes a plurality of wings (in this case 4 wings but may also be 3, 5, 6 or more) configured to rotate 360 degrees around a central longitudinal axis thereof and by its rotation to release the insects portion by portion. The rotation rate may be determined by the controller according to the released material type and the environmental conditions. According to a preferred embodiment, the wings are made of a flexible material (such as silicon or rubber, for example, having coefficient of 80 A) to assure minimal or no damage to the dispersed material (insects). Device 100', according to a preferred embodiment thereof, does not include movable shelves (such as, movable shelves 120) since the insects are gradually released (in successive portions) due to the rotation of the wings of rotating valve 160.

The rest of the elements of device 100' may be the same as those of device 100. For example, device 100' includes an insect lodging chamber 102', which may be similar to chamber 102 of device 100 and configured to hold insects prior to and/or during the scattering process. Chamber 102' includes chamber wall(s) 110' (which may be the same as chamber wall(s) 110 of device 100) defining an inner volume of chamber 102', a chamber inlet 114' which may be the same as chamber inlet 114 of device 100), at a top section thereof, configured for loading the insects and a chamber outlet 128' (which may be the same as chamber outlet 128 of device 100), at a bottom section thereof. The insects are released from chamber outlet 128' via rotating valve 160, which is associated with outlet 128'.

Device 100' further includes an electric circuitry (not shown) functionally associated with rotating valve 160, for controlling the rotation thereof.

Device 100' further includes an insect dispersion unit 130' (which may be the same as dispersion unit 130 of device 100) comprising a converging air duct 134' (which may be the same as converging air duct 134 of device 100) having an air flow inlet 138' (which may be the same as air flow inlet 138 of device 100) and an air flow outlet 142' (which may be the same as air flow outlet 142 of device 100). Chamber outlet 128' is connected to a converged section 136' (which may be the same as converged section 136 of device 100) of air duct 134', such that air flowing from air flow inlet 138' to air flow outlet 142' creates a pressure drop (venturi effect), which induces suction of insects from chamber 102', through rotating valve 160, into air duct 134' and out of the device through air flow outlet 142'. Insect dispersion unit 130' further includes a compressor 140' located in, or in proximity to, air flow inlet 138' for producing (additional) air flow from air flow inlet 138' to air flow outlet 142'.

According to some embodiments, chamber outlet 128' is connected to convergent section 136' via a chamber-to-duct passage 133' (which may be the same as chamber-to-duct passage 133 of device 100).

It is to be understood, without bounding to any theory, that the effect inducing the insect exiting the device is the venturi effect. In brief, in fluid dynamics the velocity of a fluid (or gas) must increase as it passes through a constriction while its static pressure must decrease. Hence, any gain of kinetic energy that the fluid (or gas) may attain by its increased velocity through a constriction (e.g., converged section 136' of air duct 134') is balanced by a drop in pressure, which forms the venturi effect and results in suction of the insects out of the device and into the environment.

According to some embodiments, chamber inlet 114' may be covered by a porous (not shown but may be similar to cover 116 of device 100). Such porous cover may enable exchange of oxygen/air between chamber 102' and the environment.

According to some embodiments, insect lodging chamber 102' may be integrally formed with or connected to insect dispersion unit 130'.

According to some embodiments, insect lodging chamber 102' may be modular, such that various sizes of chamber 102' can be assembled to dispersion unit 130' in order to form device 100, based on the requirement.

According to some embodiments, device 100' may further include one or more temperature regulating units 122' (shown here as three but can be any number, such as 1, 2, 3, 4 or more and may be the same as regulating units 122 of device 100) configured to regulate the temperature in chamber 102' (e.g., cool as needed). According to some embodiments, one or more temperature regulating units 122' may include a Peltier module or any other cooling/heating element(s).

According to some embodiments, device 100's temperature regulating unit 122' includes one or more temperature sensors (not shown) configured to monitor the temperature within device 100' and particularly within chamber 102', such that when a temperature above/below a desired temperature (range) is detected, temperature regulating unit 122' cools/heats chamber 102' respectively.

The predetermined density threshold includes a number of insects per cm². According to some embodiments, the predetermined density threshold is between zero insects/cm² to about 10 insects/cm². According to some embodiments, the predetermined density threshold is between about 10 insects/cm² to 100 insects/cm². According to some embodiments, the predetermined density threshold is between about 10 insects/cm² to 1000 insects/cm². The density threshold may vary depending on the insect type and its size.

According to some embodiments, the at least one density sensor comprises an optic sensor. According to some embodiments, the at least one density sensor comprises a motion sensor. According to some embodiments, the at least one density sensor comprises a sonic sensor.

According to some embodiments, device 100 may be modular, where chamber 102 can be assembled with dispersion unit 130 in order to form device 100.

According to other embodiments, chamber 102 may be integrally formed with dispersion unit 130.

According to some embodiments, device 100 further includes a separating element 132 configured to block or unblock (or partially block) chamber outlet 128 from dispersion unit 130, and a motor 126 (e.g., a servo motor) associated with separating element 132 for controlling the transition of separating element 132 from fully blocking outlet 128 to fully opening (unblocking) it, and anywhere in-between these two options, wherein the position of separating element 132 with respect to outlet 128 determines the size of the opening between chamber 102 and dispersion unit 130, and more particularly, between chamber 102 and air duct 134. Motor 126 is supported by a bracket 127, which is secured to dispersion unit 130.

According to some embodiments, the extent of opening the passage from chamber 102 to dispersion unit 130, which is determined by separating element 130, is predetermined. According to some embodiments, the separating element motor is functionally connected to the electric circuitry, such that, the electric circuitry determines the extent of opening afforded by separating element 132.

According to some embodiments, the transition of separating element 132 from fully blocking outlet 128 to fully opening (unblocking) it, and anywhere in-between these two options is performed at a slow rate, in order to afford an easy passage of insects from chamber 102 into dispersion unit 130.

Reference is now made to FIGS. 3A-3G, which schematically depict the process of releasing the insects utilizing device 300, according to some embodiments. Device 300 (which may be similar to device 100 in some respects but is simplified in order to clearly demonstrate the insect releasing process) includes an insect lodging chamber 302 configured to hold insects prior to and/or during the scattering process. Chamber 302 includes three movable shelves 320a-c (collectively 320). Device 300 further includes an insect dispersion unit 330 having a converging air duct 334 having an air flow inlet 338 and an air flow outlet 342. Chamber outlet 328 is connected to a converged section 336 of air duct 334 via a chamber-to-duct passage 333. Insect dispersion unit 330 further includes a compressor 340 located in, or in proximity to, air flow inlet 338 for producing (additional) air flow from air flow inlet 338 to air flow outlet 342.

Figures 3A, 3B:
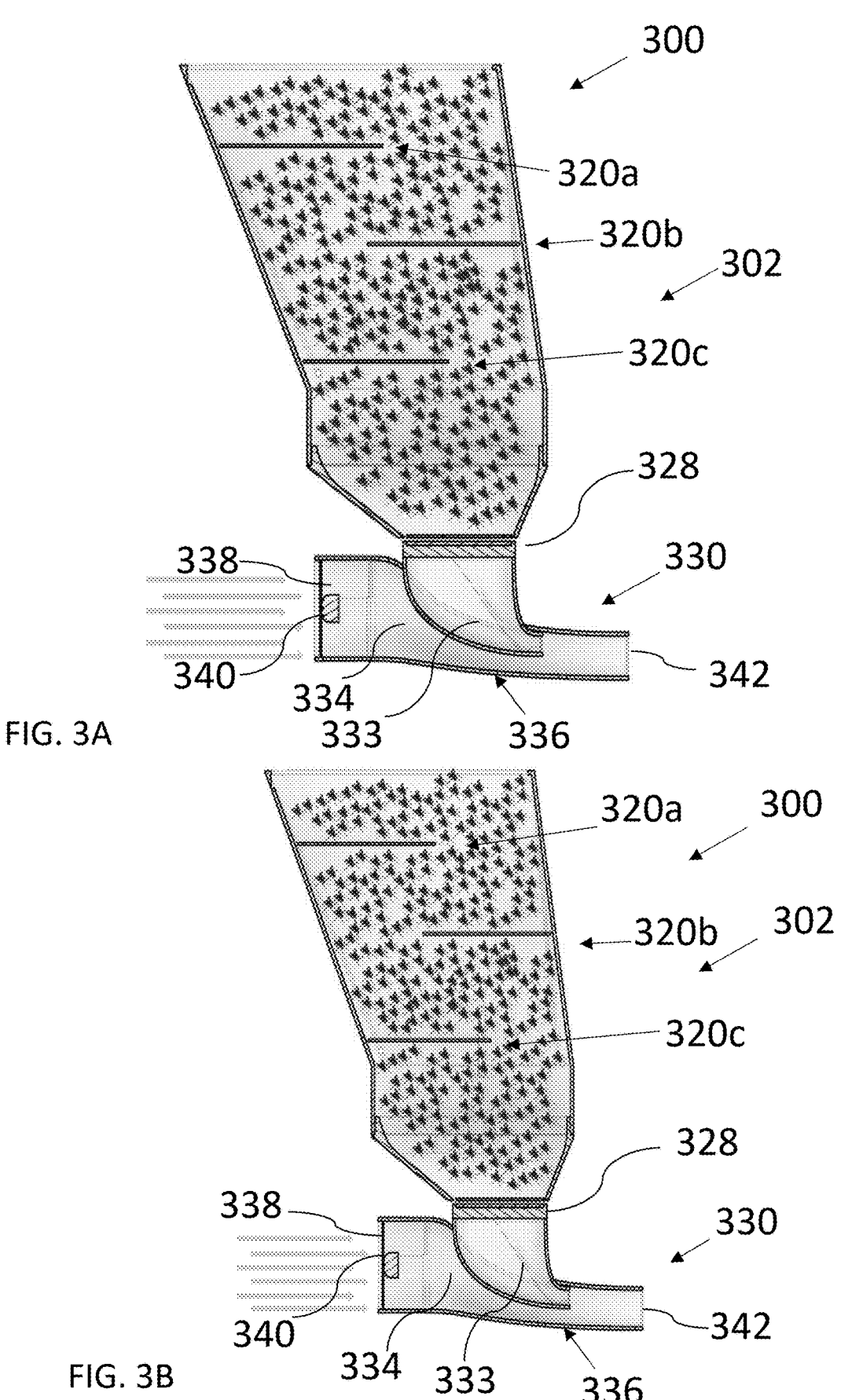
FIGS. 3A-3G schematically depict the process of releasing the insects utilizing the device, according to some embodiments.

In FIG. 3A, chamber 302 is loaded with insects, chamber outlet 328 is closed and all movable shelves 320a-c are in expanded configuration. Compressor 340 is activated, and air is shown to flow (thick arrows and broken lines) from the environment to dispersion unit 330 through air flow inlet 338 of converging air duct 334.

Figures 3C, 3D:
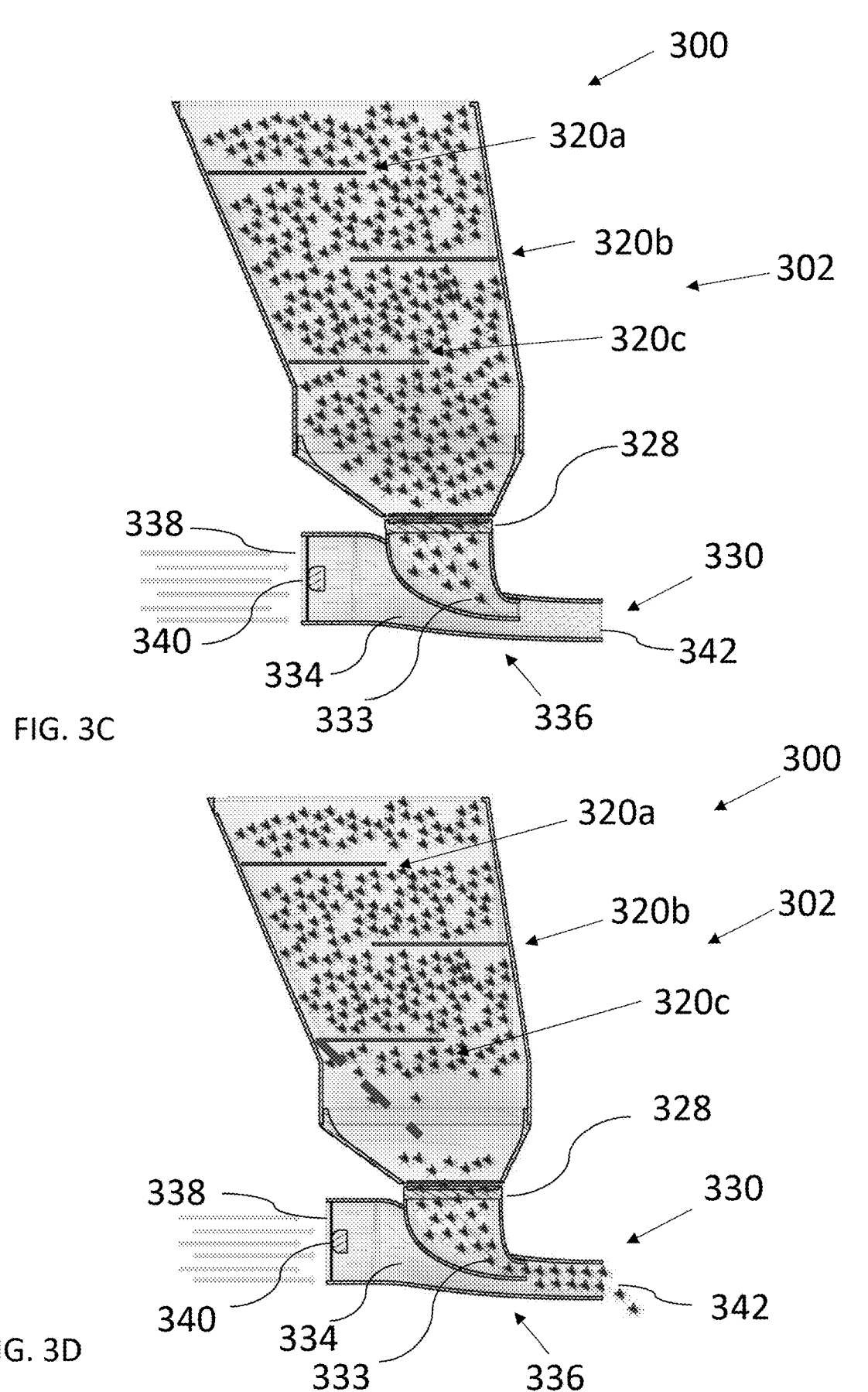

In FIG. 3B, chamber 302 is loaded with insects, chamber outlet 328 is closed and all movable shelves 320a-c are in expanded configuration. Compressor 340 is activated, and air is shown to flow (thick arrows and broken lines) from the environment to dispersion unit 330 through air flow inlet 338 of converging air duct 334. Since chamber outlet 328 is connected to converged section 336 of air duct 334, air flowing from air flow inlet 338 to air flow outlet 342 creates a pressure drop (venturi effect), which induces suction of insects from chamber 302, through chamber outlet 328, via chamber-to-duct passage 333 (FIG. 3 C) and into air duct 334 and out of the device through air flow outlet 342 (FIG. 3D). The rate of the insect suction out of device 300 may be controlled by an extent of opening a valve positioned in chamber outlet 328 and/or by the compressor force/velocity. As the insects exit device 300, the insect density in chamber 302 decreases and lower shelf 320c (closest to chamber outlet 328) is shifted from an expanded configuration to a folded configuration (represented by a dashed line), allowing the insects to move downwards faster from the upper compartments formed by shelves 320a-b to the lower compartment formerly formed by shelf 320c.

Figures 3E, 3F:
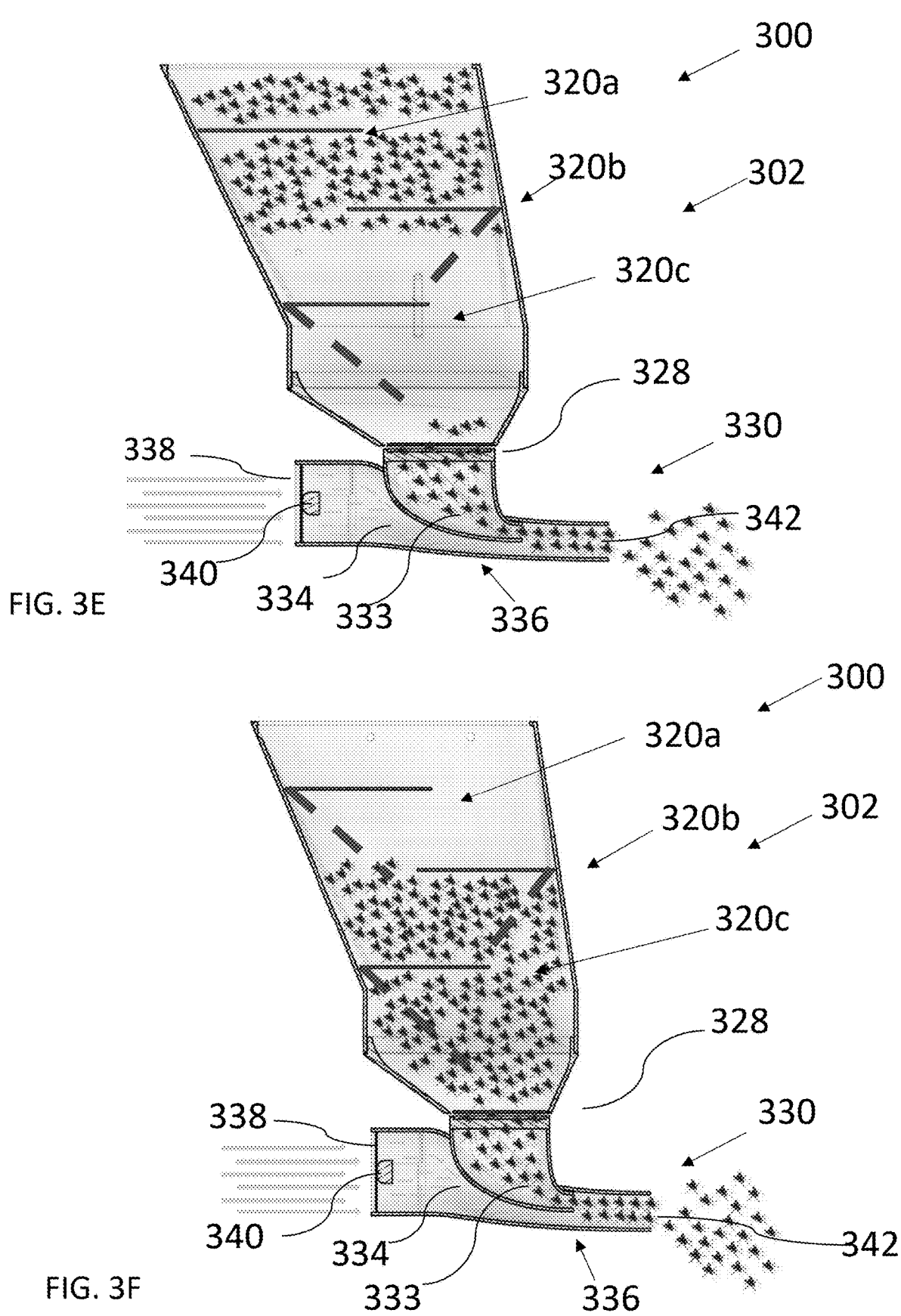
Figure 3G:
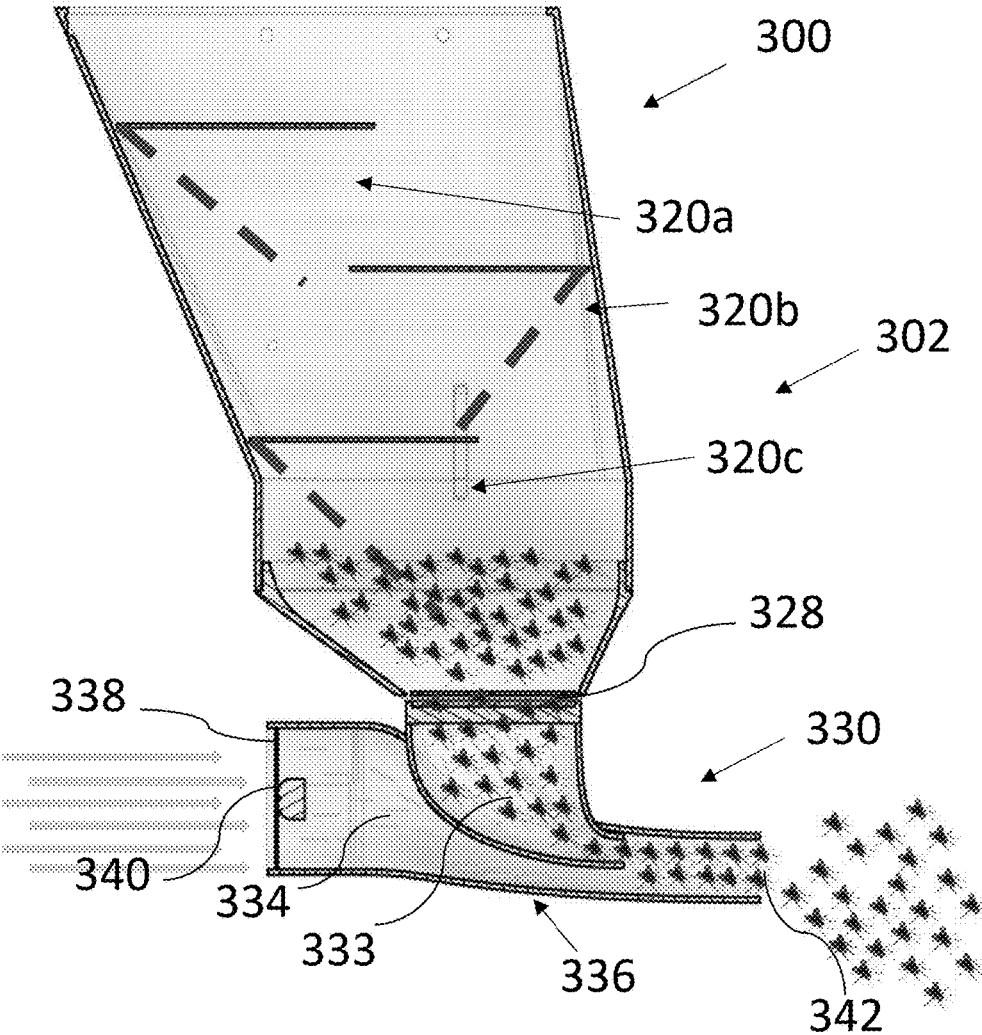

As the insects continue to exit device 300, the insect density in chamber 302 further decreases and upper shelves 320a and b are successively shifted from an expanded configuration to a folded configuration (represented by dashed lines), allowing the insects to move downwards from the upper compartments to the lower compartment (FIGS. 3E and 3F, respectively).

Figure 4:
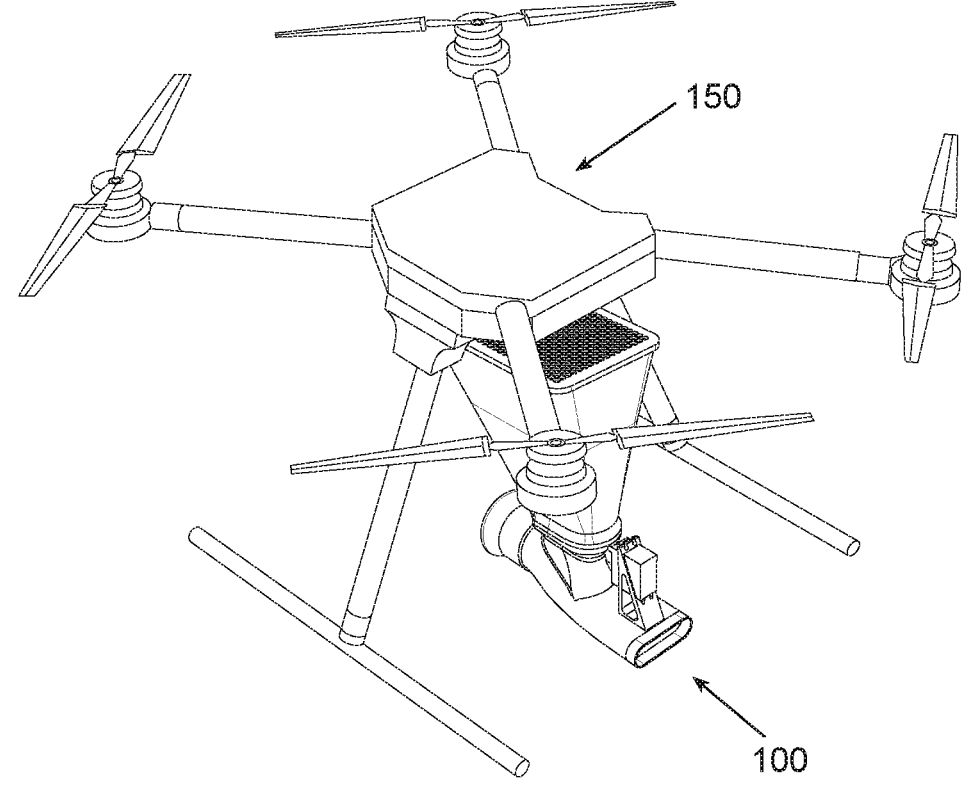
FIG. 4 schematically depicts the device connected to an aerial vehicle, according to some embodiments.

Reference is now made to FIG. 4, which schematically depicts the device 100/300 connected to an aerial vehicle 150, according to some embodiments.

Aerial vehicle 150 may be any manned or unmanned aerial vehicle such as a drone, quadcopter, and the like. Device 100/300 and/or aerial vehicle 150 may be functionally connected to a ground-based controller, and a system of communications between the two. Aerial vehicle 150 and/or device 100/300 activation may be remotely controlled and operated by a human operator or autonomously.

According to some embodiments, aerial vehicle 150 may include a navigation system (not shown). According to some embodiments, device 100/300 may include a navigation system or operate in communication with a navigation system of aerial vehicle 150. According to some embodiments, the navigation system may be located elsewhere (i.e., not on aerial vehicle 150 nor on device 100/300), using radio or other signal transmission to navigate device 100/300 attached to aerial vehicle 150. Device 100/300 may operate based on location indication obtained from the navigation system. The instructions may include, but are not limited to, location for dispersing insects and size of area to be dispersed.

The navigation system may be any suitable navigation system, including, but not limited to, a satellite navigation system, such as a global positioning system (GPS).

The term "insect" as used herein includes, in accordance with some embodiments, beneficial insects. According to some embodiments, the term "insect" as used herein includes, but is not limited to, any one or more of mosquitoes (e.g., *Anopheles*), screw-worm fly, Mexican fruit fly, Tsetse fly, Mediterranean fruit fly, Caribbean fruit fly, Queensland fruit fly, codling moth, pink bollworm, false codling moth, cactus moth, melon fly, onion fly, painted apple moth, spiders, butterflies and any other insect.

The term "plurality", as used herein, may refer to more than one (e.g., 2, 3, 4, 5 or more).

The term "unmanned aerial vehicle" may refer to a remotely operated aerial vehicle.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

Unless specifically stated otherwise, as apparent from the disclosure, it is appreciated that, according to some embodiments, terms such as "processing", "computing", "calculating", "determining", "estimating", "assessing", "gauging" or the like, may refer to the action and/or processes of a computer or computing system, or similar electronic computing device, that manipulate and/or transform data, represented as physical (e.g. electronic) quantities within the computing system's registers and/or memories, into other data similarly represented as physical quantities within the computing system's memories, registers or other such information storage, transmission or display devices.

Embodiments of the present disclosure may include apparatuses for performing the operations herein. The apparatuses may be specially constructed for the desired purposes or may include a general-purpose computer(s) selectively activated or reconfigured by a computer program stored in the computer. Such a computer program may be stored in a computer readable storage medium, such as, but not limited to, any type of disk or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method(s). The desired structure(s) for a variety of these systems appear from the description below. In addition, embodiments of the present disclosure are not described with reference to any particular programming language. It will be appreciated that a variety of programming languages may be used to implement the teachings of the present disclosure as described herein.

Aspects of the disclosure may be described in the general context of computer-executable instructions, such as program modules, being executed by a computer. Generally, program modules include routines, programs, objects, components, data structures, and so forth, which perform particular tasks or implement particular abstract data types. Disclosed embodiments may also be practiced in distributed computing environments where tasks are performed by remote processing devices that are linked through a communications network. In a distributed computing environment, program modules may be located in both local and remote computer storage media including memory storage devices.

The invention claimed is:

1. A device for releasing insects from an aerial vehicle, the device comprising:
   an insect lodging chamber configured to hold insects, the chamber comprising a chamber wall defining an inner volume of the chamber, a chamber inlet, a chamber outlet and one or more movable shelves, each shelf is attached, at a first end thereof, to an inner surface of the chamber wall, wherein each shelf has an expanded configuration and a folded configuration, wherein in the expanded configuration a shelf is extended across the chamber, wherein a second end of said shelf does not contact an opposing inner surface of the chamber, so as to facilitate free move of the insects between two sections of the chamber formed by the shelf,
   an insect dispersion unit comprising:
      a converging air duct comprising an air flow inlet and an air flow outlet, wherein the chamber outlet is connected to a converged section of air duct, such that air flowing from air flow inlet to air flow outlet creates a pressure drop, which induces suction of insects from chamber, through chamber outlet, into air duct and out of the device through air flow outlet; and
      a controller functionally associated with each shelf, for controlling the configuration thereof.

2. The device according to claim 1, wherein the diameter of the air flow outlet is smaller than the diameter of the air flow inlet.

3. The device according to claim 1, wherein the converging air is a tube structure having a first section with a first cross section area and a second section with a second cross section area, wherein the first section is upstream to the second section and the first cross section area is larger than the second cross section area.

4. The device according to claim 1, further comprising a separating element configured to block or unblock chamber outlet and a motor associated therewith for controlling the separating element so as to determine the size of an opening between the chamber and the air duct.

5. The device according to claim 1, wherein the chamber outlet is connected to converged section via a chamber-to-duct passage.

6. The device according to claim 1, further comprising a compressor located in, or in proximity to, air flow inlet for producing air flow from air flow inlet to air flow outlet.

7. The device according to claim 6, wherein the controller is further configured to control a separating element, the compressor and/or a temperature regulating unit.

8. The device according to claim 1, further comprising a temperature regulating unit for cooling the temperature of the chamber.

9. The device according to claim 1, further comprising a navigation system and/or an interface for communicating with a navigation system, for determining the location of the device and/or for controlling the operation of the device based on the location determined.

10. The device according to claim 1, wherein at least one of the one or more movable shelves is attached, at a first end thereof, to an inner surface of the chamber wall through a controllable mechanism.

11. The device according to claim 1, wherein at least one of the one or more movable shelves is designed to fold down along the chamber walls when the at least one shelf is shifted to a folded configuration.

12. The device according to claim 11, wherein at least one shelf of the one or more movable shelves is a telescopic shelf comprising a plurality of sections designed to slide into/on one another when the telescopic shelf is shifted to a folded configuration.

13. The device according to claim 1, wherein the chamber wall is coated with a thermal coating.

14. A system for releasing insects from an aerial vehicle, the system comprising:
   a device for releasing insects from an aerial vehicle, the device comprising
      an insect lodging chamber configured to hold insects, the chamber comprising a chamber wall defining an inner volume of the chamber, a chamber inlet, a chamber outlet and a one or more of movable shelves, each shelf is attached, at a first end thereof, to an inner surface of the chamber wall, wherein each shelf has an expanded configuration and a folded configuration, wherein in the expanded configuration a shelf is extended across the chamber, wherein a second end of said shelf does not contact an opposing inner surface of the chamber, so as to facilitate free move of the insects between two sections of the chamber formed by the shelf,
   an insect dispersion unit comprising:
      a converging air duct comprising an air flow inlet and an air flow outlet, wherein the chamber outlet is connected to a converged section of air duct, such that air flowing from air flow inlet to air flow outlet creates a pressure drop, which induces suction of insects from chamber, through chamber outlet, into air duct and out of the device through air flow outlet; and
   a controller functionally associated with each shelf, for controlling the configuration thereof, and
   an unmanned aerial vehicle.

15. A method for releasing insects from an aerial vehicle, the method comprising:
providing a device according to claim 6;
loading insect into the insect lodging chamber; and
utilizing a controller:
   activating the compressor,
   facilitating passage of insects between the chamber outlet and the converged section of the air duct, thereby creating a venturi effect, which induces suction of insects from the insect lodging chamber, through the chamber outlet, into the air duct and out of the device through the air flow outlet; and
   shifting at least one of the one or more shelves from an expanded configuration to a folded configuration, upon indication of a reduction in insect density in the chamber.

\* \* \* \* \*